United States Patent [19]
Gott

[11] Patent Number: 5,274,403
[45] Date of Patent: Dec. 28, 1993

[54] LENS USEFUL IN INHIBITING THE PRODUCTION OF MELATONIN AND LENS PRODUCED THEREBY

[76] Inventor: George M. Gott, 2880 N. Ashpark La., Boise, Id. 83704

[21] Appl. No.: 770,666

[22] Filed: Oct. 1, 1991

Related U.S. Application Data

[63] Continuation-in-part of Ser. No. 338,899, Apr. 17, 1989, abandoned, which is a continuation-in-part of Ser. No. 90,577, Aug. 28, 1987, abandoned.

[51] Int. Cl.$^5$ .............................................. G02C 9/00
[52] U.S. Cl. ........................................ 351/47; 351/44; 351/165
[58] Field of Search .................... 351/44, 47, 48, 165; 128/396

[56] References Cited

PUBLICATIONS

Brainard et al. "Effect of light Irradiance and Wavelength on the Syrain Hamster Reproductive System", Endocrinology,–1986.
Lewy et al. "Light Supresses Melatonin Secretion in Humans", *Science* vol. 210 Dec. 1980.
Lewy et al. "Melatonin, Light & Chronobiological Disorders", CIBA Foundation Symp., vol. 117 pp. 23-25-2,–1985.
Lewry et al. "SuperSensitivity to Light:Possible Tract Marker for Manic Depressive Illness", Am. J. Psychiatry Jun. 1985.
Doan et al. Scheduled Exposive to Daylight:A Potential Strategy to Reduce "Set Lag" following Transmeridian Flight, Psych pharmacology Blt. vol. 20 No. 3, 1984.
Lissoni et al., "A Clinical Study of the Pineal Gland Activity in Oncologic Patients", Cancer, Feb. 15, 1986.
Fevre-Montange et al., "Effects of Jetlag on Hormonal Patterns Journal of Clinical Endocrinology & Metabolism", vol. 52, No. 4, 1981.
Cardinali et al. "Pineal gland, photoperiodic responses and puberty", J. of Endocrinol. Invest 7:157,–1984.

*Primary Examiner*—Bruce Y. Arnold
*Assistant Examiner*—Hung Xuan Dang
*Attorney, Agent, or Firm*—William Bethurum

[57] ABSTRACT

A lens that transmits light expressing a transmission curve which has a low cut-in wavelength in the vicinity of 400 nm, rising gradually in terms of percentage of light transmitted, to a maximum in the vicinity of 509 nm and then descending in equal manner, in terms of wavelength and percentage of light transmitted, to a high wavelength cut-off in the vicinity of 600 nm, and method of manufacture. The overall transmission curve expresses essentially a Gaussian configuration. The transmission curve is congruent with the rod mediated portion of the electromagnetic wavelength spectrum for the human eye, also described as scotopic in character and believed to be operative in maximizing the inhibition of melatonin secretion, a substance produced by the human pineal gland.

8 Claims, 3 Drawing Sheets

LENS USEFUL IN INHIBITING THE PRODUCTION OF MELATONIN AND LENS PRODUCED THEREBY

CROSS-REFERENCE TO RELATED APPLICATIONS

This application is a continuation-in-part of Application Ser. No. 07/338,899, filed Apr. 17, 1989, which in turn is a continuation-in-part of Application Ser. No. 07/090,577, filed Aug. 28, 1987, both now abandoned.

BACKGROUND OF THE INVENTION

1. Field of the Invention

The device of the invention relates generally to optical devices, and more particularly to optical devices transmitting light having a frequency range of 400-600 nanometers. The methods of the invention relate to the use of the device in inhibiting the production of melatonin for various health conditions.

2. Description of the Prior Art

Various devices have been developed to stimulate the senses of hearing and sight or to stimulate and pattern brain function; particularly as an aid to evoke relaxation. The idea of modifying eyeglasses for therapeutic reasons other than the correction of vision has been created as typified by British Patent No. 1,142,139 issued to Luis Toha. See also "Health in Color Power", the story of light by Chromatadyne Corporation, Copyright 1939.

No device is known nor method known which is keyed to the physiological impact of light on the production of melatonin by the pineal gland, although research over the last ten to fifteen years abounds with pineal and light related research. One of the most exciting aspects of the present invention is that the therapy offers a drug free modality. Published medical research indicates that melatonin secretion levels of the pineal gland can be regulated by selectively controlling light color and intensity through the eye. See Cardinali, D. P., Vacas, M. I. "Pineal Function in Reproductive Physiology", Recent Advances in Fertility Research, Part A: Developments in Reproductive Endocrinology, p. 55-71 (1982); Cardinali, D. P., Vacas, M. I., "Pineal Gland, Photoperiodic Responses and Puberty?, J. Endocrinology Invest., 7:157-165 (1984); Daan, S., Lewy, A. J., "Scheduled Exposure to Daylight: A Potential Strategy to Reduce 'Jet Lag' Following Transmeridian Flight", Physchopharmacology Bulletin 20:566-568 (1984); Lewy, A. J. et. al., "Light Suppresses Melatonin Secretion in Humans", Science Volume 235, p. 352-354 (Jan. 16, 1987); Lewy, A. J. et. al., "Supersensitivity to Light: Possible Trait Marker for Manic-Depressive Illness", American Journal of Psychiatry, 1142:6, p.725-727 (Jun. 1985b); Lewy, A. J., et. al., "Melatonin, Light and Chronological Disorders", CIBA Foundation Symposium 117, p. 231-252 (1985a); Guyton, A. C., Textbook of Medical Physiology", Sixth Edition, Published by W. B. Saunders Co., (1981); Reiter, R. J., "Normal Patterns of Melatonin Levels in the Pineal Gland and Body Fluids of Humans and Experimental Animals", J. Neural Transm. Suppl., 21:35-54 (1986); Lissoni, Paolo et al, "A Clinical Study of the Pineal Gland Activity in Oncologic Patients", Cancer 57:837-842 (1986); and Fevre-Montange, Michelle, et. al., "Effects of 'Jet Lag' on Hormonal Patterns II. Adaption of Melatonin Circadian Periodicity", J. Clinical Endocrinol Metabolism 52:642-649 (1981). Brainard, G. C. et. al., "Dose-Response Relationship Between Light Irradiance and the Suppression of Plasma Melatonin in Human Volunteers", Brain Research, 454:212-218 (1988); Brainard G. C., et. al., "Effect of Light Wavelength on the Suppression of Nocturnal Plasma Melatonin in Normal Volunteers", Ann. N.Y. Acad. Sci., 452:376-378 (1985).

Melatonin is now known to have significant impact upon the human endocrine system. It is known as well that the primary source of melatonin is the pineal gland. Additionally, the human pineal gland is photosensitive and responds primarily to specific wavelengths of light in the visible spectrum. Inhibition of melatonin secretion in the human is dependent upon light of specific wavelength and intensity impacting the retina, and particularly the rods or the scotopic portion of visible light, (Lewy, et. al., 1985a). Light having wavelengths between 400 and 600 nanometers is recognized as most affecting the scotopic or rod mediated retinal response (Textbook of Medical Physiology, pg. 741 & FIG. 59-7, 1981) and melatonin is most effectively suppressed at those wavelengths peaking at substantially 509 nanometers, i.e., 500-520 nanometers, (Lewy, et. al., 1985a).

While it is well known that eyeglasses have been made which are operable to pass ma-y different bands of light, no eyeglasses are known which are limited to the 400-600 wavelength band; nor are eyeglasses known which have a light intensity maximizing at 509 nanometers. See "Spectral-Transmissive Properties and Use of Colored Eye-Protective Glasses" by W. W. Coblentz and R. Stair, (Jun. 1, 1938).

SUMMARY OF THE INVENTION

The present invention provides an optical device for transmitting light having wavelengths between 400-600 nanometers while blocking light of other frequencies for the suppression of melatonin in the therapeutic treatment of various health disorders. Additionally the present invention provides an optical device which maximizes the intensity of light transmitted at substantially 509 nanometers.

The present invention also provides methods of utilizing the above optical devices in the treatment of amenorrhea and dysmenorrhea, the control of ovulation, seasonal affective disorder, jet lag, and neoplastic tumor growth.

DETAILED DESCRIPTION OF THE INVENTION

Figure 1:
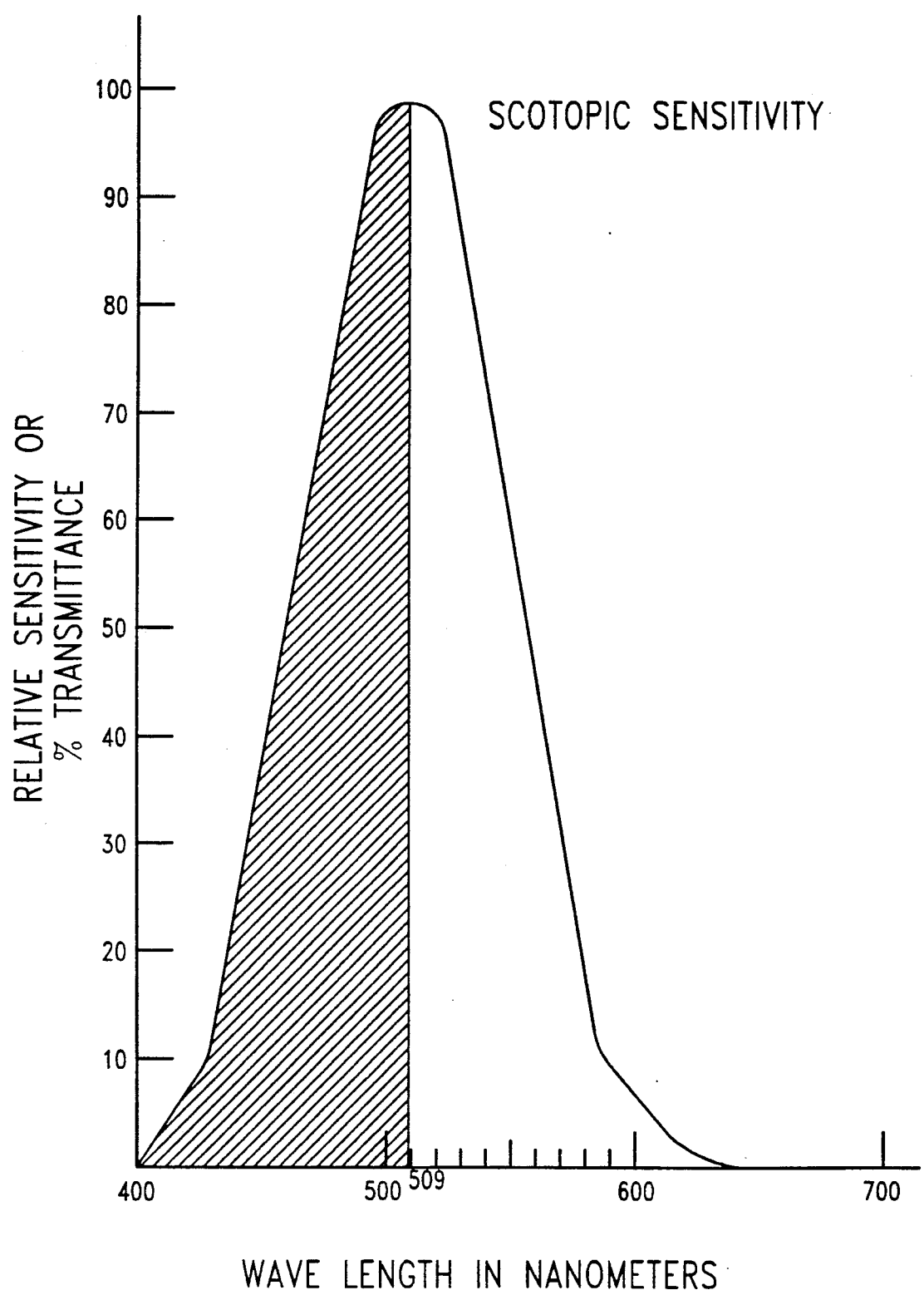
FIG. 1 is a graph depicting wavelengths of light and intensity of transmittance which maximize the suppression of melatonin produced by the pineal gland.
Figure 2:
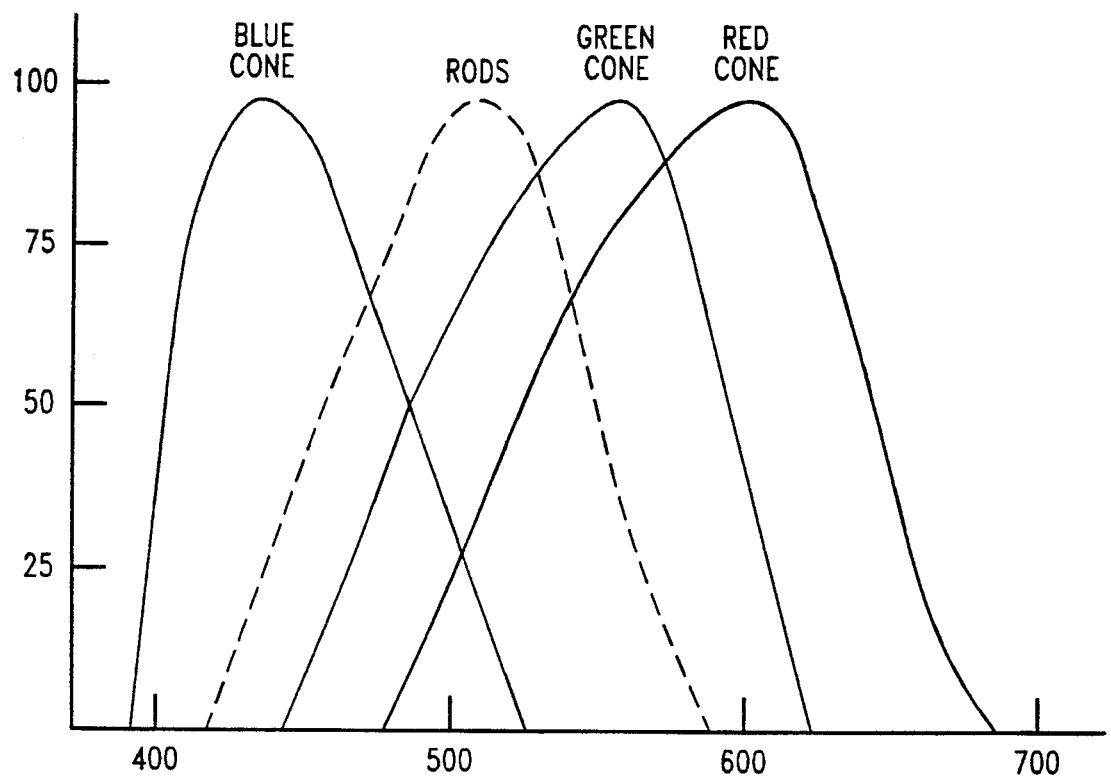
FIG. 2 is a graph depicting the peak spectral absorption curves of the blue, green, and red spectrums.
Figure 3:
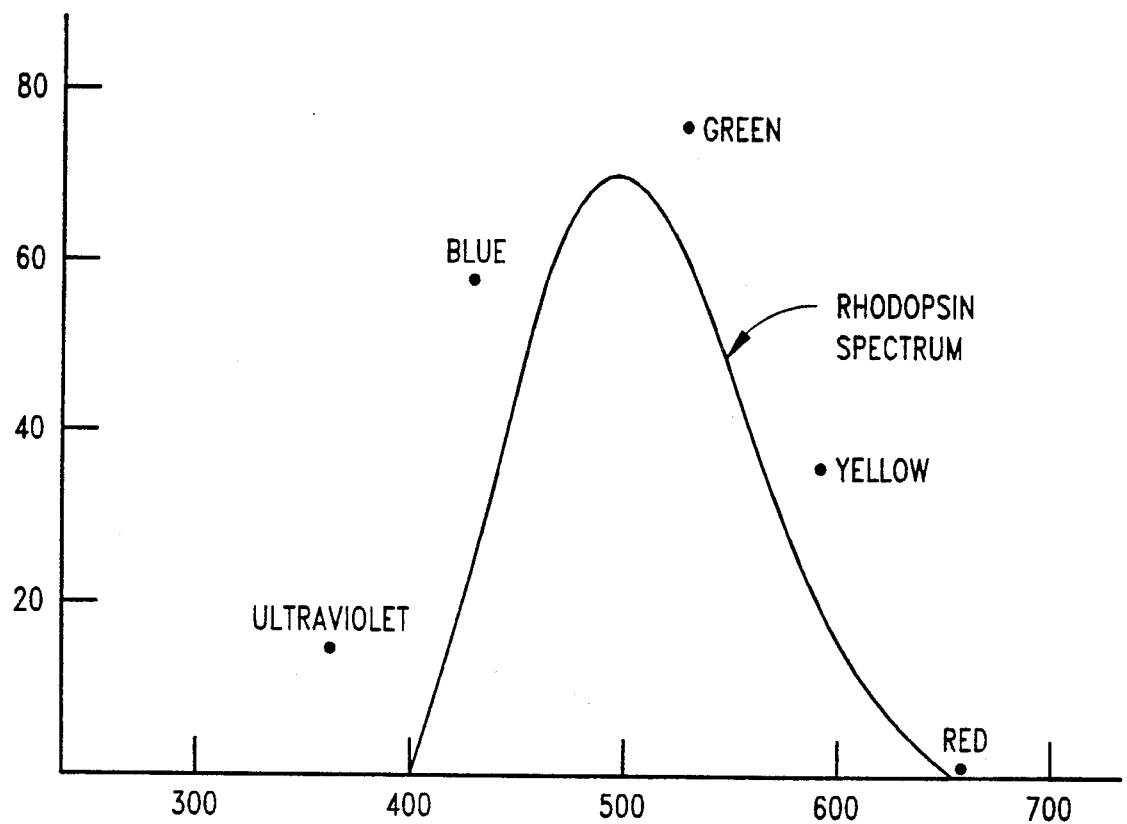
FIG. 3 is a graph illustrating the spectral dependency for suppression of pineal hydroxyindole-o-methyl transferase.

The device of the present invention may take various configurations, it being necessary that it be placed between the eye and a source of light. Contemplated structures include windows, light globes, and eyeglasses. It is critical to the invention that the device transmit only light having wavelengths in the 400-600 nanometer range; blocking light of other frequencies. (Lewy, A. J. et al 1985a, pg. 231-252). It is also highly important that the maximum intensity of the light transmitted be in the range of 500-520 nanometers and preferably at 509 nanometers. In that eyeglasses are most accessible and most convenient, it is believed that eyeglasses having the above transmission characteristics will be the preferred embodiment of the present invention. The eyeglass structure is conventional, except for the light transmitting lenses, and may be in the form of traditional monocles, spectacles, or contact lenses, including so-called "clip-ons".

In the simplest form, the lenses are constructed using conventional homogeneous clear glass or plastic materials and then treating each lens with a material designed to selectively control wavelengths of light transmitted to the retina to the lightwave range and intensity, as above stated.

The above described optical device may be effectively used in the correction of amenorrhea. Amenorrhea is defined as absence or abnormal stoppage of the menses. It is known that suppression of melatonin brings about an increase in gonadotropin activity. A tenfold rise in gonadotropin activity of urinary extracts from 11 to 14 year-old girls, corresponding to an approximate 30% seasonal increase in daily hours of sunshine, has been reported (Cardinali and Vacas, 1984). A method of maximizing exposure to those wavelengths between 400-600 nanometers and peaking substantially at 509 nanometers would therefore be beneficial in the treatment of amenorrhea and teenage amenorrhea, in particular. The method of the present invention, therefore, includes the providing of light and of sunlight, in particular; transmitting said light through an optical device having a band pass of 400-600 nanometers to the eye of the patient, thereby blocking all other frequencies, and repeating the process on a daily basis until normal menses is obtained. In that maximum suppression of melatonin is at a peak intensity of 509 nanometers, such transmission of light through the optical device is highly desired.

The above described optical device may also be used in control of the menstrual cycle for increased chance of conception. Ovulation, and its timing, is, of course, critical to conception. Serum melatonin levels play a special role in this process (Cardinali and Vacas, 1982,4). The most recent and complete study suggests that melatonin levels in the blood of young women with normal menstrual cycles are lowest at the time of ovulation, (Reiter, 1986). A method for maximizing those wavelengths of light to the retina that most inhibit melatonin production would be most helpful, therefore, in an effort to stimulate and to time ovulation. The method of the present invention to inhibit the production of melatonin to control ovulation for promoting conception therefore includes the steps of first determining time of ovulation within the normal menstrual cycle; providing light and sunlight, in particular; transmitting the light to the eye from the time of onset of menses to a period of from one to three days before a predetermined time of optimum fertility for ovulation, generally mid-cycle; and then transmitting light, having only wavelengths from 400-600, to the eye for the one to three day period immediately prior to the predetermined optimum time for ovulation, as related to peak fertility.

The device, as above described, may also be used as a method to control symptoms of depression, sleep disturbance, and weight gain associated with the disorder, commonly known as SAD, or seasonal affective disorder. Individuals may be categorized as "phase advanced" indicating those individuals having all circadian rhythms advanced, or "phase delayed" indicating those individuals whose rhythms are delayed. Phase advanced individuals typically have difficulty going to sleep but experience early morning awakening. Phase delayed people have great difficulty awakening in the early morning. After classifying the patient as either phase delayed or phase advanced, the individual is instructed to use the optical device, transmitting only those wavelengths of light between 400-600 nanometers and peaking at substantially 509 nanometers. Phase delayed individuals use the device from dawn to three hours past dawn and phase advanced individuals use it from three hours pre-dusk to dusk, Lewy. et al. 1985a) Seven to fourteen days of this regimen is considered adequate to therapeutically reset ones biological clock.

Additionally, the above described device may also be used as a method to inhibit the growth of neoplastic tumors. Melatonin is said to stimulate tumor growth in the morning and inhibit tumor growth in the late afternoon, (Lissoni, Paolo et. al., Cancer 57, pgs. 837-842, 1986). The patient is instructed to use the optical device from the time of awakening until sunset or dusk; the cycle being repeated as necessary. The procedure may be changed, as necessary, to accommodate other therapies such as chemotherapy, which seems to diminish blood melatonin levels.

For controlling the symptoms of jet lag, passengers are first classified as "phase advanced" or "phase delayed". Jet lag is intimately related to melatonin level, (Fevre-Montange, 1981). Passengers upsetting their biological clock by traveling from west to east and hence phase delayed, are instructed to use the optical device of the present invention for the period of dawn to three hours post-dawn on a daily basis, not to exceed eleven days. Those individuals traveling east to west and hence phase advanced, are instructed to use the optical device of the present invention for the period of three hours pre-dusk to dusk on a daily basis, also not to exceed eleven days.

Lens and Process Reduction-to-Practice

A standard and readily available CR-39 polymer lens was immersed in a stainless steel tank which was filled with Red Out dye using a 1:1 ratio with distilled water. The Red Out dye was identified in detail in the Gott Affidavit of the prior application filed March 25, 1991, which is incorporated herein by reference and was obtained from Brain Power Inc. of Miami, Fla. The above liquid mixture was heated to a temperature of approximately 98±1 degrees Centigrade. The lens was then immersed in the dye solution for a specific period of time dependent upon the desired percentage of light transmission desired. The time of actual immersion in the dye is dependent upon the use preferred by the wearer. Those needing a great deal of visible light, while still wishing to shift the burden of retinal work from the cones to the rods for pineal melatonin inhibition, require a relatively light tint involving an emersion time of 2 to 5 minutes. A two minute dying time is the standard for those in poorly lighted environments or those viewing computer terminals for extended periods of time.

The darker scotopic tint is used primarily for those with very sensitive eyes and those being worn outside for driving, flying, skiing or other activities that require excessive exposure to bright visual light stimulation. The darkest lenses in terms of percentage of light transmitted are produced by emersion up to 120 minutes. However, the majority of tint is absorbed after 55-60 minutes making a standard dying time for a dark scotopic lens of roughly one hour. However, small decreases in percentage of light transmission can be achieved with dying times up to two hours in duration.

The treated lens was removed from the dying tank, rinsed and dried. The transmission curve of the dyed lens was then determined using a spectrophotometer, Bausch and Lomb Model 600. Using this Bausch and Lomb spectrophotometer, I observed the transmission curve substantially as described herein and one that I sought to develop in a lens since 1986. This curve had an abrupt rise in transmission from a low wavelength cut-off in the vicinity of 400 nanometers, peaking between 500 and 510 nanometers at which there was a maximum percentage of light transmitted of 64%. Then, the curve abruptly falls off to a value in the vicinity of 600 nanometers which defines the high wavelength cut-off for my scotopic lens. After the lenses dyed they were edged by standard edging machines well known in the ophthalmic industry. The lenses were then mounted in metal or plastic frames suitable for eyewear.

Having thus described in detail a preferred embodiment of the present invention, it is to be appreciated and will be apparent to those skilled in the art that many physical changes could be made in the apparatus lens and method described herein without altering the inventive concepts and principles embodied therein. The present embodiments are therefore to be considered in all respects as illustrative and not restrictive, the scope of the invention being indicated by the appended claims rather than by the foregoing description, and all changes which come within the meaning and range of equivalency of the claims are therefore to be embraced therein.

I claim:

1. A lens, said lens for use in an eyeglass frame, article of manufacture or other light transmitting device, said lens having a wavelength selective coating disposed thereon and a light transmittance versus wavelength characteristic which peaks in the vicinity of 509 nanometers and which has a low wavelength cut-in in the vicinity of 400 nanometers and a high wavelength cut-off in the vicinity of 600 nanometers, whereby the user's eye is exposed to the scotopic wavelength range of light which is operative to maximize the inhibition of melatonin, a substance produced by the human pineal gland.

2. The lens defined in claim 1 wherein said wavelength selective coating transmits light of maximum intensity in the wavelength range of 500 nanometers to 520 nanometers.

3. The lens defined in claim 1 wherein said coating includes a chosen dye.

4. The lens defined in claim 3 wherein said chosen dye is a Red Out dye.

5. An eyeglass lens operative to maximize the inhibition of melatonin, a substance produced by the human pineal gland, said lens having a coating thereon which imparts to said lens a light transmittance versus wavelength characteristic which peaks in the vicinity of 509 nanometers and which has a low wavelength cut-in in the vicinity of 400 nanometers and a wavelength cut-off in the vicinity of 600 nanometers.

6. A lens having a wavelength selective coating disposed thereon which transmits light of maximum intensity in the wavelength range of 500 nanometers to 520 nanometers and a light transmittance versus wavelength characteristic which peaks in the vicinity of 509 nanometers and which has a low wavelength cut-off in the vicinity of 400 nanometers and a high wavelength cut-off in the vicinity of 600 nanometers.

7. The lens defined in claim 6 wherein said wavelength selective coating includes a chosen dye.

8. The lens defined in claim 7 wherein said chosen dye is a Red out dye.

* * * * *